United States Patent
Park (10) Patent No.: US 10,231,699 B2
(45) Date of Patent: Mar. 19, 2019

(54) ULTRASONIC WAVE-DISSIPATION BLOCK AND ULTRASONIC PROBE HAVING SAME

(71) Applicant: HUMANSCAN CO.,LTD, Ansan-si, Gyeonggi-do (KR)

(72) Inventor: Wonseop Park, Seoul (KR)

(73) Assignee: HUMANSCAN CO., LTD, Ansan-si, Gyeonggi-do (KR)

( * ) Notice: Subject to any disclaimer, the term of this patent is extended or adjusted under 35 U.S.C. 154(b) by 129 days.

(21) Appl. No.: 15/383,661

(22) Filed: Dec. 19, 2016

(65) Prior Publication Data

US 2017/0095227 A1 Apr. 6, 2017

Related U.S. Application Data

(63) Continuation of application No. PCT/KR2015/000942, filed on Jan. 29, 2015.

(30) Foreign Application Priority Data

Jun. 19, 2014 (KR) .................. 10-2014-0074724

(51) Int. Cl.
*G01N 29/24* (2006.01)
*A61B 8/00* (2006.01)
(Continued)

(52) U.S. Cl.
CPC .............. *A61B 8/4281* (2013.01); *A61B 8/00* (2013.01); *A61B 8/4444* (2013.01); *G01N 29/24* (2013.01);
(Continued)

(58) Field of Classification Search
CPC ..... A61B 8/4281; A61B 8/4444; G01N 29/24
See application file for complete search history.

(56) References Cited

U.S. PATENT DOCUMENTS 4,683,396 A * 7/1987 Takeuchi .............. B06B 1/0622
310/357
2005/0075571 A1 4/2005 Barnes
(Continued)

FOREIGN PATENT DOCUMENTS

| JP | 2010-042093 A | 2/2010 |
|---|---|---|
| JP | 2011-528929 A | 12/2011 |
| KR | 10-2010-0132367 A | 12/2010 |
| KR | 10-1018626 B1 | 3/2011 |

OTHER PUBLICATIONS

International Search Report dated Apr. 21, 2015 for PCT/KR2015/000942, citing the above reference(s).
(Continued)

*Primary Examiner* — Xin Y Zhong
(74) *Attorney, Agent, or Firm* — Hauptman Ham, LLP (57) ABSTRACT

The present invention provides an ultrasonic wave-dissipation block and an ultrasonic probe having the same, which reflect and diffract a backward ultrasonic wave progressing toward the rear of piezoelectric ceramics for generating ultrasonic waves, so as to dissipate the ultrasonic wave, thereby improving the absorption performance of the ultrasonic wave, while reducing the weight and size of a part performing the role of absorbing the ultrasonic wave. The ultrasonic wave-dissipation block comprises: a base body in which an accommodation space is formed; and an ultrasonic reflector disposed in the accommodation space of the base body, and reflecting the ultrasonic wave, flowing in from the outside of the base body, in the direction of the inner sides of side walls of the base body.

14 Claims, 7 Drawing Sheets

(51) Int. Cl.
G10K 11/28 (2006.01)
B06B 1/06 (2006.01)
G10K 11/168 (2006.01)
(52) U.S. Cl.
CPC ............... *G10K 11/28* (2013.01); *B06B 1/06* (2013.01); *G10K 11/168* (2013.01)

(56) References Cited

U.S. PATENT DOCUMENTS

| | | |
|---|---|---|
| 2007/0157404 A1 | 7/2007 | Brewer et al. |
| 2008/0139945 A1* | 6/2008 | Hu .......................... A61B 8/00 600/459 |
| 2011/0114303 A1* | 5/2011 | Rhim ....................... A61B 8/00 165/185 |
| 2011/0152691 A1* | 6/2011 | Ikeda ....................... A61B 8/00 600/459 |
| 2013/0342077 A1 | 12/2013 | Lautzenhiser et al. |

OTHER PUBLICATIONS

Japanese Office Action dated Nov. 6, 2017 in connection with the counterpart Japanese Patent Application No. 2016-573505, citing the above reference(s).

European Search Report dated Apr. 20, 2017 by European Patent Office in connection with the counterpart European Patent Application No. 15809960.6, citing the above reference(s).

\* cited by examiner

ULTRASONIC WAVE-DISSIPATION BLOCK AND ULTRASONIC PROBE HAVING SAME

CROSS REFERENCE TO RELATED APPLICATION

The present application is a continuation of International Patent Application No. PCT/KR2015/000942, filed Jan. 29, 2015, which is based upon claims the benefit of priority to Korean Patent Application No. 10-2014-0074724, filed on Jun. 19, 2014. The disclosure of the above-listed applications is hereby incorporated by reference herein in its entirety.

TECHNICAL FIELD

The present invention relates to an ultrasonic wave-dissipation block and an ultrasonic probe having the same, and more particularly, to an ultrasonic wave-dissipation block and an ultrasonic probe having the same, which reflect and diffract a backward ultrasonic wave advancing toward a rear of piezoelectric ceramics for generating an ultrasonic wave so that the ultrasonic wave is dissipated, thereby improving acoustic characteristics.

BACKGROUND ART

Ultrasonic waves are widely used to inspect the inside of a human body or an animal or to measure a solid such as metal or plastic in a non-destructive manner A device for generating ultrasonic waves is manufactured in the form of a probe (hereinafter, referred to as an "ultrasonic probe") which is easy for an operator to hold by hand.

An ultrasonic probe includes piezoelectric ceramics for generating ultrasonic waves and a sound absorbing block that is disposed on a rear surface of the piezoelectric ceramics and absorbs a backward ultrasonic wave advancing toward the rear of the piezoelectric ceramics.

The sound absorbing block adjusts and improves acoustic characteristics of a forward ultrasonic wave advancing toward the front of the piezoelectric ceramics by absorbing the backward ultrasonic wave advancing toward the rear of the piezoelectric ceramics.

A sound absorbing block of a conventional ultrasonic probe is realized by disposing a sound absorbing material having a block shape behind piezoelectric ceramics, and when a size of the sound absorbing block is increased to improve a sound absorbing property, a size of an ultrasonic probe is excessively increased or a weight of the ultrasonic probe is increased.

DISCLOSURE

Technical Problem

The present invention is directed to providing an ultrasonic wave-dissipation block and an ultrasonic probe having the same, which reflect and diffract a backward ultrasonic wave advancing toward a rear of piezoelectric ceramics for generating an ultrasonic wave so that the ultrasonic wave is dissipated, thereby improving an ultrasonic sound absorbing property while reducing a weight and size.

Technical Solution

One aspect of the present invention provides an ultrasonic wave-dissipation block including: a base body in which an accommodation space is formed; and an ultrasonic reflector that is disposed in the accommodation space of the base body and reflects ultrasonic waves introduced from an outside of the base body in a direction toward an inner surface of a side wall of the base body.

Here, the base body may be formed in a cylindrical shape having an open upper portion, and the ultrasonic reflector may include a metal plate for reflecting the ultrasonic waves.

Also, diffraction slits for diffracting the ultrasonic waves may be formed on the side wall of the base body.

Also, the diffraction slits may be formed in parallel or in different directions, and may be formed in a straight shape or a cross shape on the side wall.

Also, at least one side wall of the base body may be formed, and the ultrasonic reflector may be formed in any one of a conical shape or a polygonal conical shape to correspond to a shape of the side wall.

Also, a plurality of diffraction slits for diffracting at least a part of the ultrasonic waves toward an inside of the ultrasonic reflector may be formed on a side wall of the ultrasonic reflector.

Also, an ultrasonic absorbing member for absorbing the ultrasonic waves may be formed on at least one of an outer surface of the ultrasonic reflector and an inner surface of the ultrasonic reflector opposing the outer surface.

Also, the ultrasonic wave-dissipation block may further include a heat transfer pattern that is formed on an outer surface of the base body.

Also, an angle between an inner surface of the base body and a side wall of the ultrasonic reflector may be an acute angle.

Another aspect of the present invention provides an ultrasonic probe including: an ultrasonic probe unit that includes an ultrasonic generating unit generating ultrasonic waves, an acoustic matching layer disposed on an upper surface of the ultrasonic generating unit, and an acoustic lens disposed on an upper surface of the acoustic matching layer; and an ultrasonic wave-dissipation block that includes a base body supporting the ultrasonic generating unit of the ultrasonic probe unit and having an accommodation space formed therein, and an ultrasonic reflector coupled to an inner surface of a side wall of the base body to reflect the ultrasonic waves in a direction toward an inner surface of the base body.

Here, diffraction slits for diffracting the ultrasonic waves reflected from the ultrasonic reflector may be formed on the side wall of the base body.

Also, the diffraction slits may be formed in parallel or in different directions, and may be formed in a straight shape or a cross shape.

Also, a plurality of diffraction slits for diffracting at least a part of the ultrasonic waves toward an inside of the ultrasonic reflector may be formed on a side wall of the ultrasonic reflector.

Also, an ultrasonic absorbing member for absorbing the ultrasonic waves may be formed on at least one of an outer surface of the ultrasonic reflector and an inner surface of the ultrasonic reflector opposing the outer surface.

Also, the ultrasonic probe may further include a flexible circuit board that is disposed between the ultrasonic wave-dissipation block and the ultrasonic generating unit to provide power to the ultrasonic generating unit, wherein a negative electrode terminal of the ultrasonic generating unit is connected to a connection terminal of the flexible circuit board.

Also, a heat transfer pattern for transmitting heat generated at the ultrasonic generating unit to the base body is formed on an outer surface of the base body.

Advantageous Effect

According to the present invention, an ultrasonic wave-dissipation block and an ultrasonic probe having the same can reflect and diffract a backward ultrasonic wave advancing toward the rear of piezoelectric ceramics for generating an ultrasonic wave so that the ultrasonic wave is dissipated, thereby improving an ultrasonic sound absorbing property while reducing a weight and size of a portion serving to absorb an ultrasonic wave.

MODES OF THE INVENTION

Hereinafter, preferred embodiments of the present invention will be described in detail with reference to the accompanying drawings. In the following detailed description of the present invention, concrete description on related functions or constructions will be omitted when it is deemed that the functions and/or constructions may unnecessarily obscure the gist of the present invention.

Terms and phrases used in the following description and claims are not to be construed as limited to ordinary or dictionary meanings, but should be construed as having meanings and concepts matching the technical ideas of the present invention based on the principle that the present inventors may properly define their own invention with concepts of terms and phrases explained in best ways. Accordingly, embodiments described in the specification and elements shown in the drawings are illustrative only and do not cover all of the technical ideas of the present invention. Therefore, it should be understood that these embodiments and elements may be replaced with different equivalents and modifications at a point of time of filing the present application.

Figure 1:
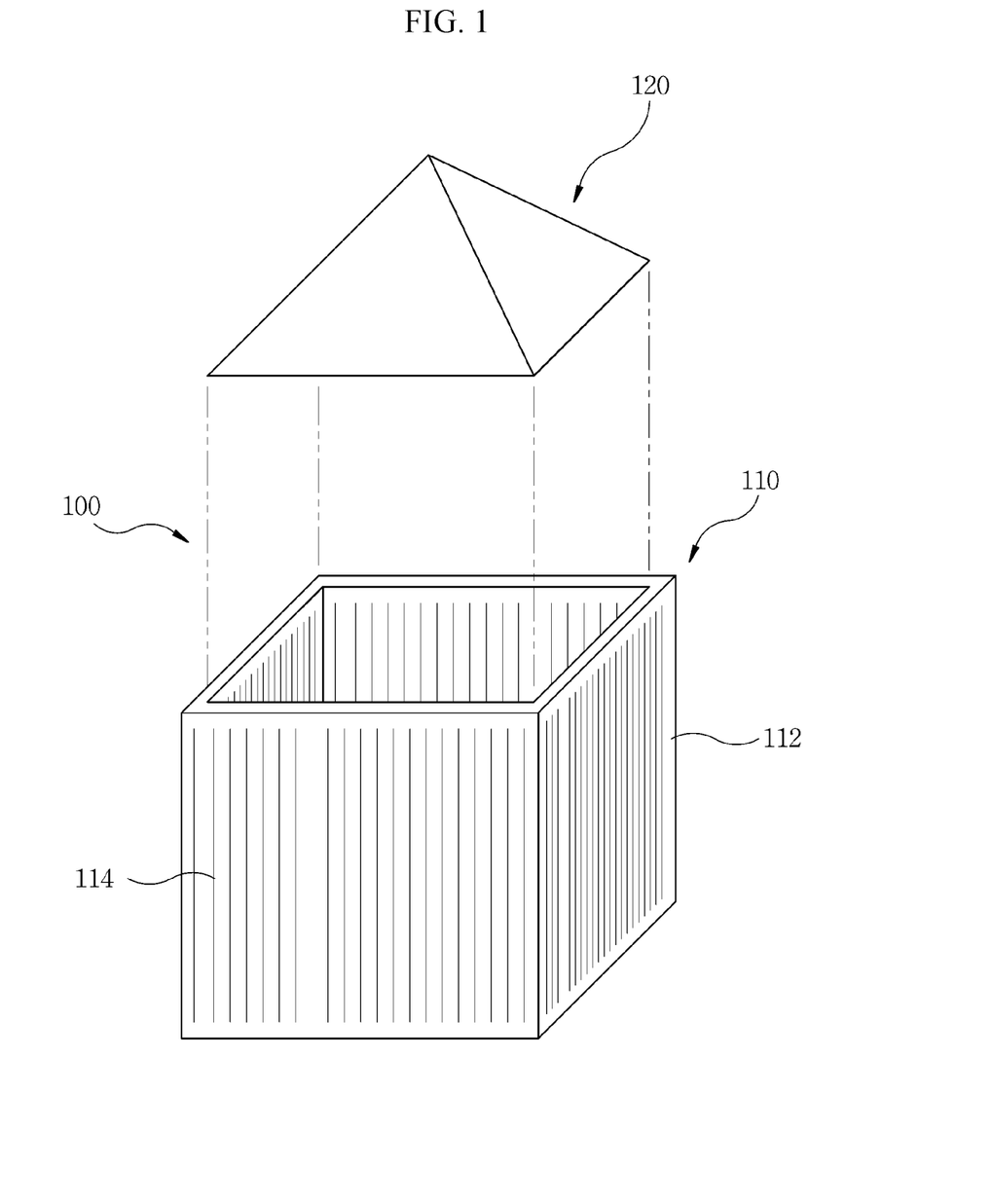
FIG. 1 is an exploded perspective view showing an ultrasonic wave-dissipation block according to an embodiment of the present invention.
Figure 2:
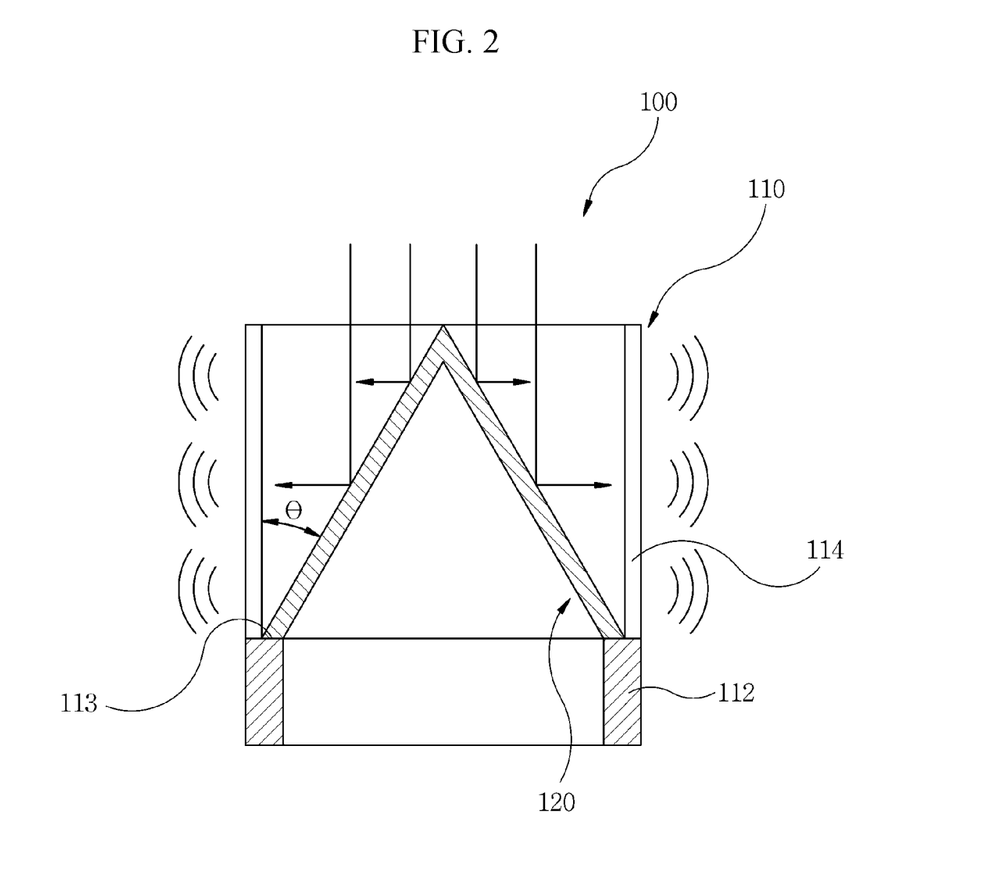
FIG. 2 is a vertical cross-sectional view showing the ultrasonic wave-dissipation block of FIG. 1 after the ultrasonic wave-dissipation block of FIG. 1 is assembled.

FIG. 1 is an exploded perspective view showing an ultrasonic wave-dissipation block according to an embodiment of the present invention, and FIG. 2 is a vertical cross-sectional view showing the ultrasonic wave-dissipation block of FIG. 1 after the ultrasonic wave-dissipation block of FIG. 1 is assembled.

Referring to FIGS. 1 and 2, an ultrasonic wave-dissipation block 100 includes a base body 110 and an ultrasonic reflector 120.

An accommodation space may be formed inside the base body 110, and the base body 110 may be formed by processing a metal plate that reflects ultrasonic waves.

Although the base body 110 is described as being a metal plate that reflects ultrasonic waves according to an embodiment of the present invention, the base body 110 may alternatively be made of a material that absorbs ultrasonic waves.

The base body 110 may be formed in a cylindrical shape such that at least one side thereof is open so that ultrasonic waves generated from an outside thereof may be introduced therein.

The base body 110 may be formed, for example, in a cylindrical shape in which an upper end thereof is open or the upper end and a lower end thereof facing the upper end are all open.

The base body 110 may include, for example, a side wall 112 that forms the accommodation space, and according to an embodiment of the present invention, there may be at least one side wall 112 of the base body 110.

When there is one side wall 112 of the base body 110, the base body 110 may be formed in a cylindrical shape, and when there are at least two side walls 112 of the base body 110, the base body 110 may be formed in a polygonal shape having at least one edge.

According to an embodiment of the present invention, the base body 110 may be formed in, for example, a rectangular tube shape having four side walls 112.

Although the base body 110 is shown as being formed in a rectangular tube shape according to an embodiment of the present invention, the base body 110 may be formed in a cylindrical shape, a pentagonal shape, or a hexagonal shape.

Diffraction slits 114 having a slit shape are formed on the side wall 112 of the base body 110. The diffraction slits 114 may be all formed on each of the side wall 112 of the base body 110.

Each of the diffraction slits 114 is formed in a shape of an opening passing through an inner surface of the side wall 112 of the base body 110 and an outer surface thereof opposing the inner surface, and each of the diffraction slits 114 is formed, for example, in a rectangular shape.

The diffraction slits 114 may be formed in a structure suitable for diffracting ultrasonic waves advancing toward the side wall 112 of the base body 110, and for example, the diffraction slits 114 formed on the side wall 112 of the base body 110 may be formed with a width of half of a wavelength of the ultrasonic waves.

A formation direction of the diffraction slits 114 formed on the side wall 112 of the base body 110 may be provided in a direction suitable for diffracting the ultrasonic waves advancing toward the side wall 112 of the base body 110.

According to an embodiment of the present invention, each of the diffraction slits 114 may be formed in a long stripe shape in a direction from an upper end of the side wall 112 of the base body 110 to a lower end thereof, and a plurality of diffraction slits 114 may be formed to be parallel to each other. Alternatively, the diffraction slits 114 may be formed in a direction parallel to the ground with respect to the ground.

Figure 3:
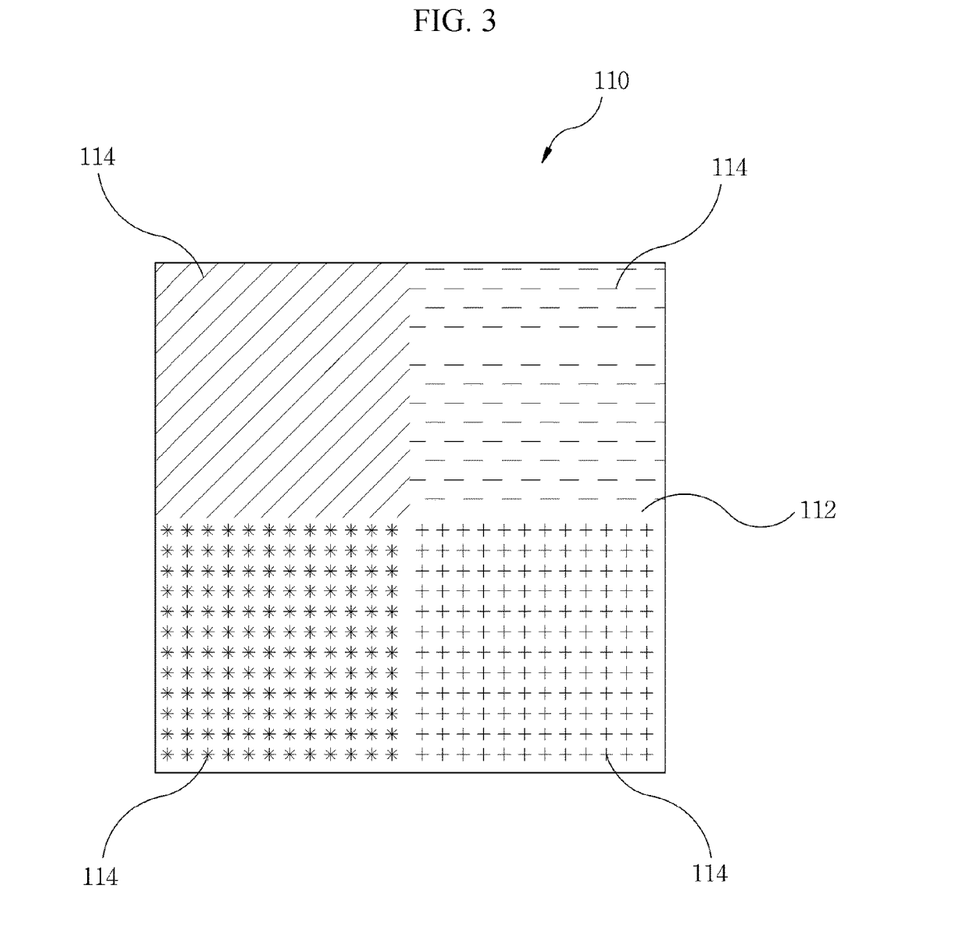
FIG. 3 is a side view showing other embodiments of a diffraction slit formed in a base body of an ultrasonic wave-dissipation block.

FIG. 3 is a side view showing other embodiments of a diffraction slit formed in a base body of an ultrasonic wave-dissipation block.

Referring to FIG. 3, the diffraction slits 114 formed on the side walls 112 of the base body 110 may be formed in a direction that is inclined with respect to the ground.

The diffraction slits 114 formed on the side wall 112 of the base body 110 may be intermittently formed on the side wall 112 along a longitudinal direction or a width direction of the side wall 112.

In addition, each of the diffraction slits 114 formed on the side wall 112 of the base body 110 may be formed in a straight shape, a cross shape, or a radial shape on the side wall 112. Further, although not shown, each of the diffraction slits 114 formed on the side wall 112 of the base body 110 may be formed in a spiral shape.

Referring again to FIGS. 1 and 2, ultrasonic waves introduced into the base body 110 should be refracted or reflected in a direction toward the side wall 112 of the base body 110 in order to diffract the ultrasonic waves introduced into the base body 110 by the diffraction slits 114 formed on the side wall 112 of the base body 110 and dissipate the diffracted ultrasonic waves.

Referring again to FIG. 1, the ultrasonic reflector 120 may be formed or disposed inside the base body 110 or coupled thereto in order to reflect or refract the ultrasonic waves introduced into the base body 110 in a direction toward the diffraction slits 114 formed on the side wall 112 of the base body 110.

The ultrasonic reflector 120 is made of a material suitable for reflecting or refracting ultrasonic waves. For example, the ultrasonic reflector 120 may be formed by processing a metal plate with a thin thickness having high ultrasonic reflectance.

The ultrasonic reflector 120 may be formed in a shape suitable for being inserted into the base body 110 and fixed inside the base body 110.

When the base body 110 is formed in, for example, a cylindrical shape, the ultrasonic reflector 120 may be formed in, for example, a circular cone shape.

When the base body 110 is formed in a rectangular tube shape, the ultrasonic reflector 120 may be formed in, for example, a quadrangular pyramid shape.

Alternatively, the base body 110 and the ultrasonic reflector 120 may be manufactured in such a way as to not correspond to each other, but in this case, a lower end of the ultrasonic reflector 120 may be fabricated to be coupled to an inner surface of the base body 110.

In order to maintain a state in which the ultrasonic reflector 120 disposed inside the base body 110 is stably disposed in the base body 110, a step 113 that supports the lower end of the ultrasonic reflector 120 may be formed on the inner surface of the side wall 112 of the base body 110.

The ultrasonic reflector 120 may be coupled to the side wall 112 of the base body 110 by welding or the like while being supported by the step 113 formed on the side wall 112 of the base body 110.

Referring again to FIG. 1, an angle θ between a side wall 122 of the ultrasonic reflector 120 and the side wall 112 of the base body 110 may be an acute angle, and the angle between the side wall 122 of the ultrasonic reflector 120 and the side wall 112 of the base body 110 may preferably be about 45 degrees.

According to an embodiment of the present invention, a length of the ultrasonic wave-dissipation block 100 may be increased when the angle between the side wall 122 of the ultrasonic reflector 120 and the side wall 112 of the base body 110 is smaller than about 45 degrees, and a width, instead of the length, of the ultrasonic wave-dissipation block 100 may be increased when the angle between the side wall 122 of the ultrasonic reflector 120 and the side wall 112 of the base body 110 is larger than about 45 degrees, and therefore the angle between the side wall 122 of the ultrasonic reflector 120 and the side wall 112 of the base body 110 may preferably be about 45 degrees.

Although the angle between the side wall 122 of the ultrasonic reflector 120 and the side wall 112 of the base body 110 is described as being about 45 degrees, the angle between the side wall 122 of the ultrasonic reflector 120 and the side wall 112 of the base body 110 may be more or less than 45 degrees according to characteristics and an appearance of an ultrasonic probe unit.

Although the separated ultrasonic reflector 120 is shown and described as being coupled to the side wall 112 of the base body 110 according to an embodiment of the present invention, the ultrasonic reflector 120 may alternatively be formed by bending a part of the side wall 112 of the base body 110.

Figure 4:
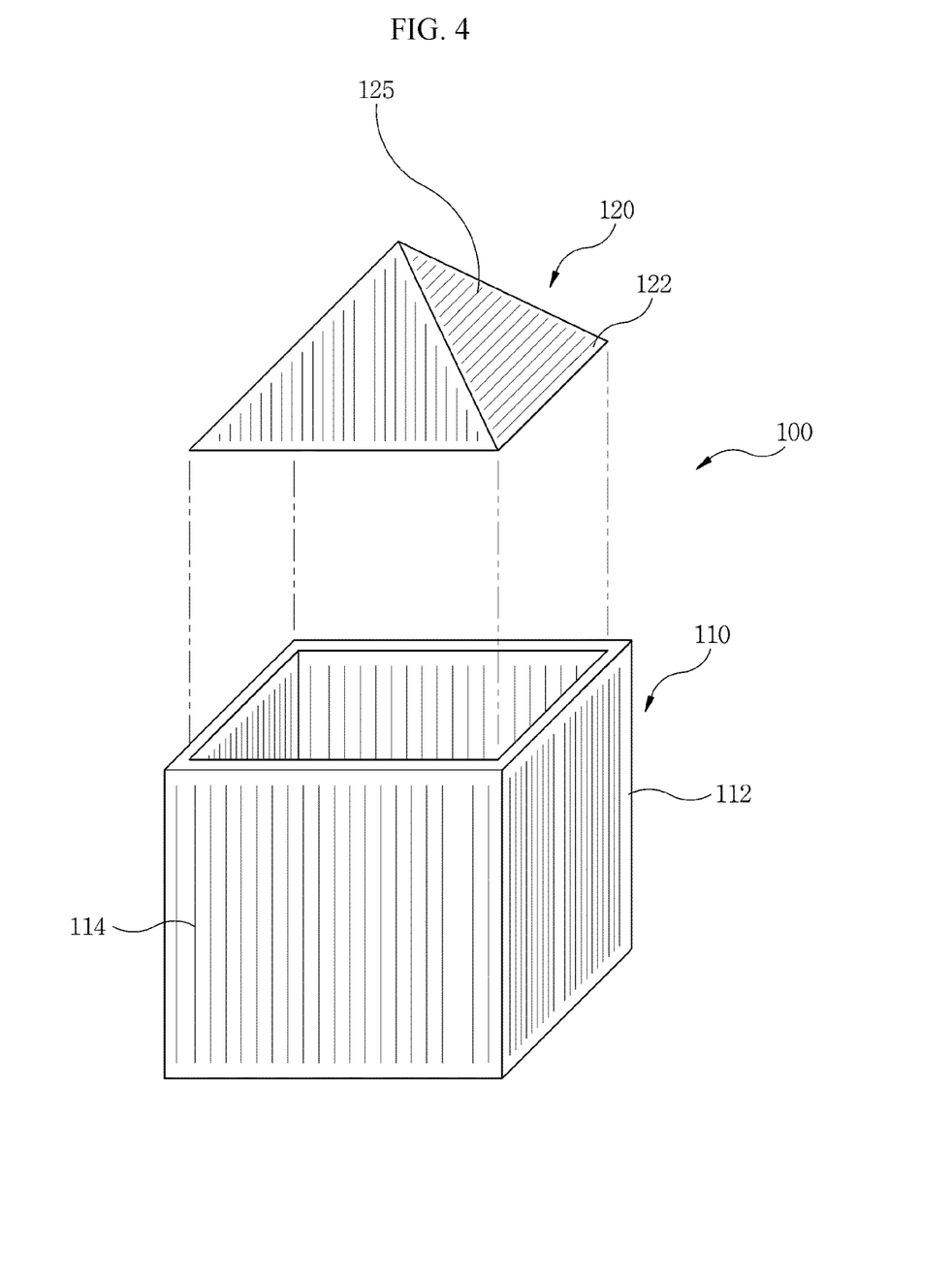
FIG. 4 is an exploded perspective view showing another embodiment of an ultrasonic reflector of an ultrasonic wave-dissipation block.

FIG. 4 is an exploded perspective view showing another embodiment of an ultrasonic reflector of an ultrasonic wave-dissipation block.

Referring to FIG. 4, the ultrasonic reflector 120 of the ultrasonic wave-dissipation block 100 may serve to reflect or refract a part of ultrasonic waves introduced into the base body 110 in a direction toward the inner surface of the side wall 112 of the base body 110, and may serve to diffract and dissipate the remaining part of the ultrasonic waves introduced into the base body 110.

Among the ultrasonic reflectors 120 shown in FIG. 4, diffraction slits 125 are formed on each side wall 122 of the ultrasonic reflector 120 that reflects and refracts the ultrasonic waves introduced into the base body 110.

Each of the diffraction slits 125 formed on each side wall 122 of the ultrasonic reflector 120 is formed in a shape of an opening passing through an inner surface of the side wall 122 of the ultrasonic reflector 120 and an outer surface thereof opposing the inner surface, and each of the diffraction slits 125 formed on the ultrasonic reflector 120 is formed, for example, in a rectangular shape.

The diffraction slits 125 formed on the ultrasonic reflector 120 may be formed in a structure suitable for diffracting the ultrasonic waves introduced into the base body 110, and for example, the diffraction slits 125 formed on the side wall 122 of the ultrasonic reflector 120 may be formed with a width of half of a wavelength of the ultrasonic waves.

In addition, a formation direction of the diffraction slits 125 formed on the side wall 122 of the ultrasonic reflector 120 may be provided in a direction suitable for diffracting the ultrasonic waves introduced into the base body 110.

Each of the diffraction slits 125 of the ultrasonic reflector 120 may be formed in a long stripe shape on the side wall 122 of the ultrasonic reflector 120, and a plurality of diffraction slits 125 may be provided to be parallel to each other. Alternatively, the diffraction slits 125 formed on the ultrasonic reflector 120 may be formed in various directions.

Meanwhile, the diffraction slits 125 formed on the ultrasonic reflector 120 and the diffraction slits 114 formed on the side wall 112 of the base body 110 may be formed in the same direction. Alternatively, the diffraction slits 125 formed on the ultrasonic reflector 120 and the diffraction slits 114 formed on the side wall 112 of the base body 110 may be formed in different directions.

The diffraction slits 125 formed on the ultrasonic reflector 120 may be formed in various shapes such as a stripe shape, a straight shape, a cross shape, a radial shape, and the like.

The ultrasonic reflector 120 shown in FIG. 4 may primarily diffract and dissipate at least a part of the ultrasonic waves introduced into the base body 110 using the diffraction slits 125, and ultrasonic waves which are not dissipated by the ultrasonic reflector 120 may be reflected or refracted in a direction from the ultrasonic reflector 120 to the side wall 112 of the base body 110 and secondarily diffracted and dissipated by the diffraction slits 115 formed on the side wall 112 of the base body 110.

Figure 5:
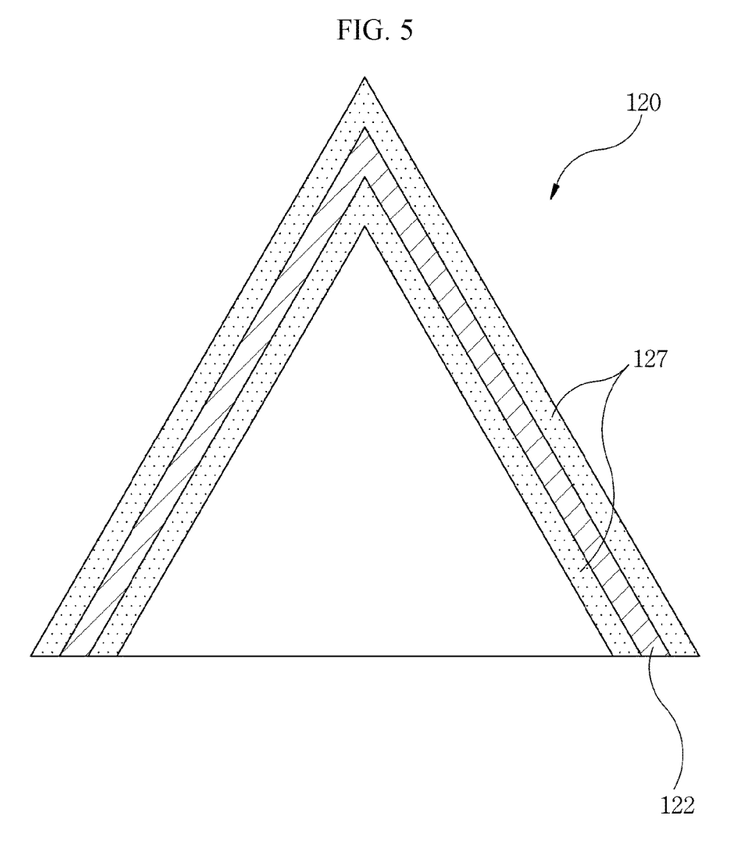
FIG. 5 is an exploded perspective view showing still another embodiment of an ultrasonic reflector of an ultrasonic wave-dissipation block.

FIG. 5 is an exploded perspective view showing still another embodiment of an ultrasonic reflector of an ultrasonic wave-dissipation block.

Referring to FIGS. 2 and 5, the ultrasonic reflector 120 of the ultrasonic wave-dissipation block 100 may be a member at which the ultrasonic waves introduced into the base body 110 directly arrive, and in FIG. 5, an ultrasonic absorbing member 127 may be formed on the outer surface of the side wall 122 of the ultrasonic reflector 120.

The ultrasonic absorbing member 127 may be formed to have a thin thickness so that a weight and volume of the ultrasonic wave-dissipation block 100 are not increased, and the ultrasonic waves introduced into the base body 110 may be absorbed and primarily dissipated by the ultrasonic absorbing member 127, and ultrasonic waves which are not absorbed by the ultrasonic absorbing member 127 may be reflected or refracted from the ultrasonic reflector 120 and diffracted and dissipated by the diffraction slits 114 formed on the side wall 112 of the base body 110.

Although the ultrasonic absorbing member 127 is described as being formed to have a thin thickness on the outer surface of the ultrasonic reflector 120 according to an embodiment of the present invention, when the diffraction slits 125 are formed on the side wall 122 of the ultrasonic reflector 120 as shown in FIG. 4, the ultrasonic absorbing member 127 may alternatively be formed even on the inner surface of the side wall 122 of the ultrasonic reflector 120 opposing the outer surface thereof as shown in FIG. 5.

Figure 6:
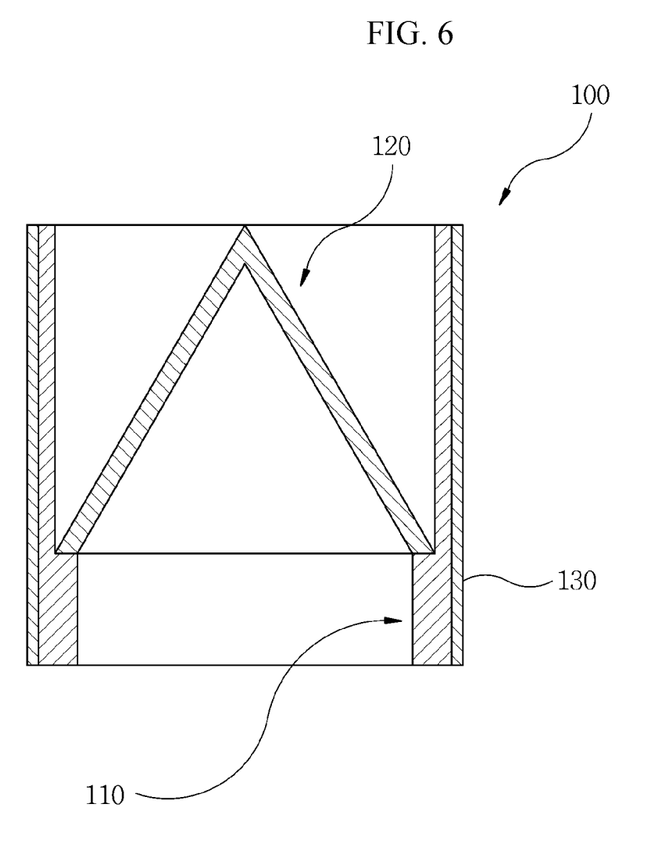
FIG. 6 is a cross-sectional view showing another embodiment of an ultrasonic wave-dissipation block.

FIG. 6 is a cross-sectional view showing another embodiment of an ultrasonic wave-dissipation block. The ultrasonic wave-dissipation block according to the embodiment of the present invention shown in FIG. 6 has substantially the same configuration as the ultrasonic wave-dissipation block 100 shown and described in FIGS. 1 and 2 except for a heat transfer pattern. Therefore, a repeated description of the same configuration will be omitted, and the same names and the same reference numerals will be given to the same configurations.

Referring to FIG. 6, the ultrasonic wave-dissipation block 100 includes the base body 110, the ultrasonic reflector 120, and a heat transfer pattern 130.

The ultrasonic-wave dissipation block 100 is coupled to an ultrasonic generator for generating ultrasonic waves and serves to dissipate an ultrasonic wave advancing backward from the ultrasonic generator. Here, a large amount of heat is generated at the ultrasonic generator while the ultrasonic generator generates ultrasonic waves, and the heat generated at the ultrasonic generator greatly reduces performance and efficiency of the ultrasonic generator.

Accordingly, the heat transfer pattern 130 is formed on an outer surface of the side wall 112 of the base body 110 in order to rapidly radiate the heat generated at the ultrasonic generator.

The heat transfer pattern 130 is particularly suitable for radiating the heat generated at the ultrasonic generator when the base body 110 is made of a non-metallic material.

Alternatively, when the base body 110 is made of a metallic material, the heat transfer pattern 130 may be made of a material having thermal conductivity higher than that of the base body 110 so that the heat generated at the ultrasonic generator may be more quickly radiated to the outside, thereby preventing deterioration of the performance of the ultrasonic generator.

The heat transfer pattern 130 may be formed in various shapes such as a band shape or a lattice shape when viewed in a plane, and one side of the heat transfer pattern 130 extends to an upper surface of the base body 110 so that the heat transfer pattern 130 may be brought into contact with the ultrasonic generator, and thereby the ultrasonic generator and the heat transfer pattern 130 may be electrically insulated from each other.

Although the heat transfer pattern 130 and the ultrasonic generator are shown and described as being electrically insulated from each other according to an embodiment of the present invention, the heat transfer pattern 130 may alternatively be electrically grounded with the ultrasonic generator.

Figure 7:
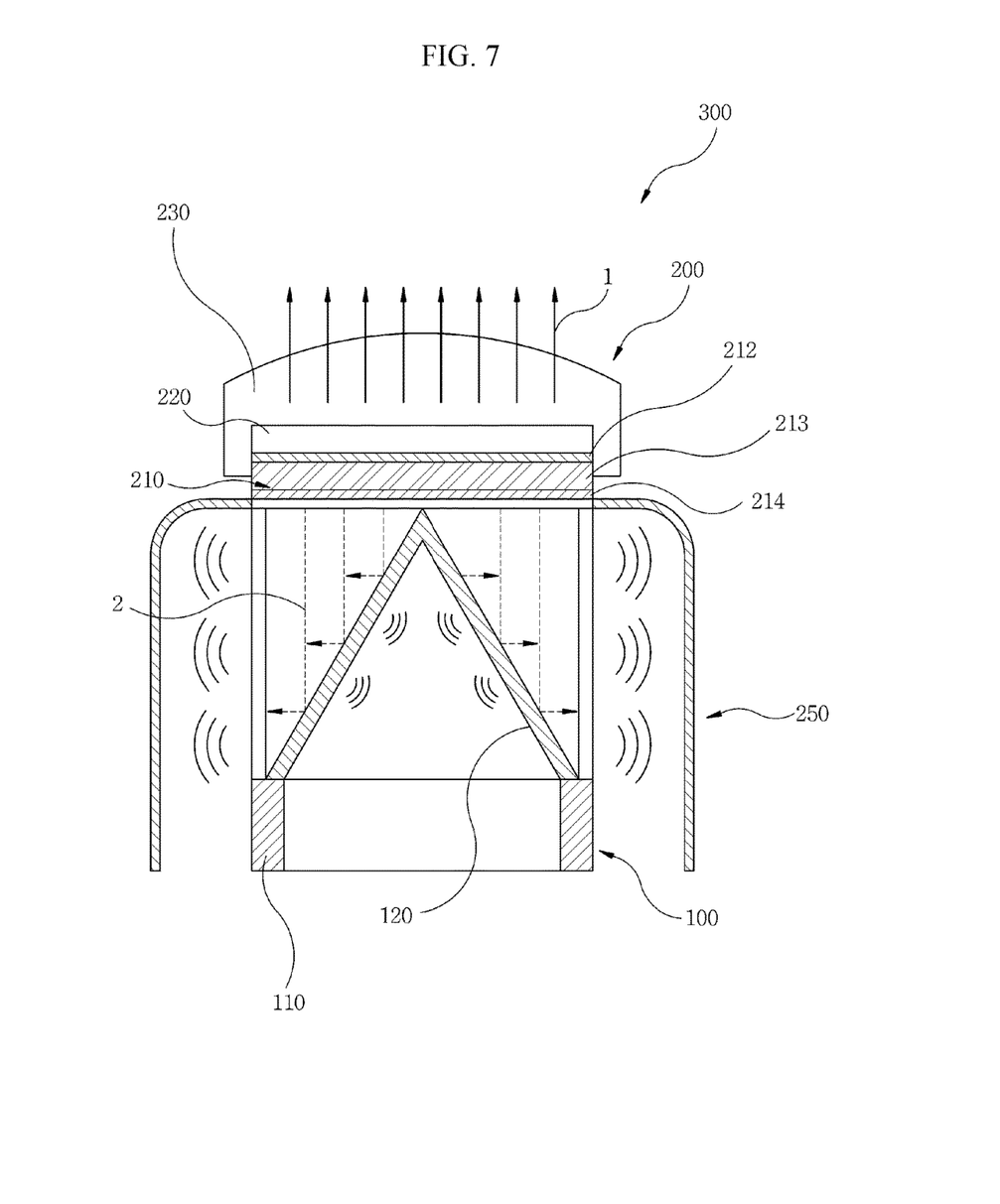
FIG. 7 is a cross-sectional view showing an ultrasonic probe having the ultrasonic wave-dissipation block shown in FIG. 1.

FIG. 7 is a cross-sectional view showing an ultrasonic probe having the ultrasonic wave-dissipation block shown in FIG. 1. According to an embodiment of the present invention, the ultrasonic wave-dissipation block 100 has substantially the same configuration as the ultrasonic wave-dissipation block 100 shown and described in FIGS. 1 to 6. Therefore, the same names and the same reference numerals will be given to the same configurations, and a repeated description of the same configuration will be omitted.

Referring to FIG. 7, an ultrasonic probe 300 includes the ultrasonic wave-dissipation block 100 and an ultrasonic probe unit 200. In addition, the ultrasonic probe 300 may further include a flexible circuit board 250.

The ultrasonic probe unit 200 is coupled to the ultrasonic wave-dissipation block 100 shown in FIGS. 2 to 6.

The ultrasonic probe unit 200 includes an ultrasonic generating unit 210, an acoustic matching layer 220, and an acoustic lens layer 230.

The ultrasonic generating unit 210 of the ultrasonic probe unit 200 generates ultrasonic waves.

According to an embodiment of the present invention, the ultrasonic generating unit 210 may include piezoelectric ceramics for generating ultrasonic waves. Although the ultrasonic generating unit 210 is shown and described as including the piezoelectric ceramics according to an embodiment of the present invention, various devices for generating ultrasonic waves may alternatively be used as the ultrasonic generating unit 210.

The ultrasonic generating unit 210 converts an externally applied electrical signal into an ultrasonic wave that is an acoustic signal and transmits the ultrasonic wave toward an object, and converts an ultrasonic reflection signal reflected back from the object in the air into an electrical signal again.

The ultrasonic generating unit 210 may be made of a ceramic material such as PZT or a single crystal material such as PMN_PT.

The ultrasonic generating unit 210 includes a positive electrode 212 to which an electrical signal is applied, a negative electrode 214, and an ultrasonic generating body 213.

The acoustic matching layer 220 may be formed on electrodes of ultrasonic wave transmitting and receiving surfaces of the ultrasonic generating unit 210 to increase reflectance and efficiency of the ultrasonic waves. Here, the acoustic matching layer 220 may be formed of at least two layers to increase the reflectance and efficiency of the ultrasonic waves.

The acoustic lens layer 230 is disposed on an upper portion of the acoustic matching layer 220, and focuses a transmitted ultrasonic wave to enhance a resolution of an ultrasonic image and provides a focused ultrasonic wave to a subject.

Silicon and the like may be given as an example of a material that may be used as the acoustic lens layer 230.

In order to apply an electrical signal to the ultrasonic generating unit 210 and process an ultrasonic reflection signal applied to the ultrasonic generating unit 210, the flexible circuit board 250 is disposed between the ultrasonic wave-dissipation block 100 and the ultrasonic generating unit 210, and the ultrasonic generating unit 210 is electrically connected to the flexible circuit board 250.

According to an embodiment of the present invention, a connection pattern is formed on each of an upper surface of the flexible circuit board 250 and a lower surface thereof opposing the upper surface. Here, the connection pattern formed on the upper surface of the flexible circuit board 250 is connected to the positive electrode 212 of the ultrasonic generating unit 210, and the connection pattern formed on the lower surface of the flexible circuit board 250 is electrically connected to the negative electrode 214 of the ultrasonic generating unit 210 and the ultrasonic wave-dissipation block 100.

Hereinafter, an operation of the ultrasonic probe 300 according to an embodiment of the present invention will be described as follows.

Referring to FIG. 7, ultrasonic waves generated from the ultrasonic generating unit 210 of the ultrasonic probe unit 200 may advance toward a front surface of the ultrasonic generating unit 210 and a rear surface thereof opposing the front surface. Here, the ultrasonic wave directed toward the front surface of the ultrasonic generating unit 210 is defined as a forward ultrasonic wave 1, and the ultrasonic wave directed toward the rear surface of the ultrasonic generating unit 210 is defined as a backward ultrasonic wave 2.

The forward ultrasonic wave 1 is directed toward an object to be inspected while the backward ultrasonic wave 2 is directed in a direction opposite the object to be inspected.

When the backward ultrasonic wave 2 is reflected and directed in the direction in which the forward ultrasonic wave 1 advances, acoustic characteristics are adversely affected.

According to an embodiment of the present invention, the ultrasonic wave-dissipation block 100 is disposed behind the ultrasonic generating unit 210 to absorb or dissipate the backward ultrasonic wave 2.

The ultrasonic reflector 120 of the ultrasonic wave-dissipation block 100 reflects or refracts the backward ultrasonic wave 2 in a direction toward the inner surface of the base body 110.

The backward ultrasonic wave 2 reflected or refracted toward the inner surface of the base body 110 by the ultrasonic reflector 120 of the ultrasonic wave-dissipation block 100 is diffracted and dissipated by the diffraction slits 114 formed on the side wall 112 of the base body 110.

According to an embodiment of the present invention, an ultrasonic absorbing member that absorbs the backward ultrasonic wave 2 or diffraction slits that diffract the backward ultrasonic wave 2 may be formed on the ultrasonic reflector 120 of the ultrasonic wave-dissipation block 100.

In this manner, the backward ultrasonic wave 2 absorbed or reflected by the ultrasonic reflector 120 of the ultrasonic wave-dissipation block 100 may be diffracted by the diffraction slits 114 of the base body 110 so that the backward ultrasonic wave 2 is dissipated, thereby further improving acoustic characteristics of the ultrasonic probe 300.

As described above, the ultrasonic wave-dissipation block and the ultrasonic probe having the same may reflect and diffract a backward ultrasonic wave advancing toward the rear of the ultrasonic generating unit for generating an ultrasonic wave so that the ultrasonic wave is dissipated, thereby improving an ultrasonic sound absorbing property while reducing the weight and size of the portion serving to absorb the ultrasonic wave.

Although a few embodiments of the present invention have been shown and described, those skilled in the art should appreciate that changes may be made to these embodiments without departing from the principles and spirit of the disclosure, the scope of which is defined in the claims and their equivalents.

INDUSTRIAL APPLICABILITY

The ultrasonic wave-dissipation block and the ultrasonic probe according to the present invention can be used in a medical instrument field using ultrasonic waves, a non-destructive inspection field using ultrasonic waves, and the like.

The invention claimed is:

1. An ultrasonic wave-dissipation block comprising:
   a base body in which an accommodation space is formed; and
   an ultrasonic reflector that is disposed in the accommodation space of the base body and reflects ultrasonic waves introduced from an outside of the base body in a direction toward an inner surface of a side wall of the base body,
   wherein diffraction slits for diffracting the ultrasonic waves are formed on the side wall of the base body.

2. The ultrasonic wave-dissipation block according to claim 1, wherein the base body is formed in a cylindrical shape having an open upper portion, and the ultrasonic reflector includes a metal plate for reflecting the ultrasonic waves.

3. The ultrasonic wave-dissipation block according to claim 1, wherein the diffraction slits are formed in parallel or in different directions, and are formed in a straight shape or a cross shape on the side wall.

4. The ultrasonic wave-dissipation block according to claim 1, wherein at least one side wall of the base body is formed, and the ultrasonic reflector is formed in any one of a conical shape or a polygonal conical shape to correspond to a shape of the side wall.

5. The ultrasonic wave-dissipation block according to claim 1, wherein a plurality of diffraction slits for diffracting at least a part of the ultrasonic waves toward an inside of the ultrasonic reflector are formed on a side wall of the ultrasonic reflector.

6. The ultrasonic wave-dissipation block according to claim 1, wherein an ultrasonic absorbing member for absorbing the ultrasonic waves is formed on at least one of an outer surface of the ultrasonic reflector and an inner surface of the ultrasonic reflector opposing the outer surface.

7. The ultrasonic wave-dissipation block according to claim 1, further comprising:
   a heat transfer pattern that is formed on an outer surface of the base body.

8. The ultrasonic wave-dissipation block according to claim 1, wherein an angle between an inner surface of the base body and a side wall of the ultrasonic reflector is an acute angle.

9. An ultrasonic probe comprising:
an ultrasonic probe unit that includes an ultrasonic generating unit generating ultrasonic waves, an acoustic matching layer disposed on an upper surface of the ultrasonic generating unit, and an acoustic lens disposed on an upper surface of the acoustic matching layer; and
an ultrasonic wave-dissipation block that includes a base body supporting the ultrasonic generating unit of the ultrasonic probe unit and having an accommodation space formed therein, and an ultrasonic reflector coupled to an inner surface of a side wall of the base body to reflect the ultrasonic waves in a direction toward an inner surface of the base body,
wherein diffraction slits for diffracting the ultrasonic waves reflected by the ultrasonic reflector are formed on the side wall of the base body.

10. The ultrasonic probe according to claim 9, claim wherein the diffraction slits are formed in parallel or in different directions, and are formed in a straight shape or a cross shape.

11. The ultrasonic probe according to claim 9, wherein a plurality of diffraction slits for diffracting at least a part of the ultrasonic waves toward an inside of the ultrasonic reflector are formed on a side wall of the ultrasonic reflector.

12. The ultrasonic probe according to claim 9, wherein an ultrasonic absorbing member for absorbing the ultrasonic waves is formed on at least one of an outer surface of the ultrasonic reflector and an inner surface of the ultrasonic reflector opposing the outer surface.

13. The ultrasonic probe according to claim 9, further comprising:
a flexible circuit board that is disposed between the ultrasonic wave-dissipation block and the ultrasonic generating unit to provide power to the ultrasonic generating unit,
wherein a negative electrode terminal of the ultrasonic generating unit is connected to a connection terminal of the flexible circuit board.

14. The ultrasonic probe according to claim 9, wherein a heat transfer pattern for transmitting heat generated at the ultrasonic generating unit to the base body is formed on an outer surface of the base body.

* * * * *